United States Patent [19]

Eberhard

[11] Patent Number: 5,068,882

[45] Date of Patent: Nov. 26, 1991

[54] DUAL PARALLEL CONE BEAM CIRCULAR SCANNING TRAJECTORIES FOR REDUCED DATA INCOMPLETENESS IN THREE-DIMENSIONAL COMPUTERIZED TOMOGRAPHY

[75] Inventor: Jeffrey W. Eberhard, Schenectady, N.Y.

[73] Assignee: General Electric Company, Schenectady, N.Y.

[21] Appl. No.: 572,590

[22] Filed: Aug. 27, 1990

[51] Int. Cl.$^5$ .............................................. G01B 15/06
[52] U.S. Cl. ......................................... 378/4; 378/9; 378/11; 378/15
[58] Field of Search ....................... 378/4, 9, 147, 149, 378/109, 110, 112, 62, 22, 18, 10, 19, 15, 11

[56] References Cited

U.S. PATENT DOCUMENTS

| | | | |
|---|---|---|---|
| 4,672,651 | 6/1987 | Horiba et al. | 378/62 |
| 4,752,691 | 6/1988 | Hawman | 378/10 |
| 4,942,596 | 7/1990 | Eberhard et al. | 378/109 |
| 4,958,081 | 9/1990 | Malmin et al. | 378/147 |

OTHER PUBLICATIONS

"The Dynamic Spatial Reconstructor", R. A. Robb et al., J. Med. Syst., vol. 4, No. 2, pp. 253–288 (1980).
"Iterative Three-Dimensional Reconstruction from Twin-Cone Beam Projections", M. Schlindwein, IEEE Trans. Nucl. Sci., vol. NS-25, No. 5, pp. 1135–1143 (Oct. 1978).
"Convolutional Reconstruction from Cone-Beam Projection Data", GN Minerbo., IEEE Trnas. Nucl. Sci., vol. NS-26, No. 2, pp. 2682–2684 (Apr. 1979).
"An Inversion Formula for Cone-Beam Reconstruction", H. K. Tuy, Siam J. Math., vol. 43, No. 3, pp. 456–552 (Jun. 1983).
"Practical Cone-Beam Algorithm", L. A. Feldkamp et al., J. Opt. Soc. Am. A., vol. 1, No. 6, pp. 612–619 (Jun. 1984).
"Image Reconstruction from Cone-Beam Projections" Necessary and Sufficient Conditions and Reconstruction Methods, B. D. Smith, IEEE Trans. Med. Imag., vol. MI–44, pp. 14–25 (Mar. 1985).
"Quantitative Cone-Beam Construction", H. Hu et al., SPIE Medical Imaging III: Image Processing, vo. 1092, pp. 492–501 (1989).

Primary Examiner—Janice A. Howell
Assistant Examiner—Kim-Kwok Chu
Attorney, Agent, or Firm—Paul R. Webb, II; James C. Davis, Jr.

[57] ABSTRACT

A configuration of three-dimensional cone beam computerized tomography imaging which minimizes the incompleteness of the data set acquired, while providing fast data acquisition to minimize motion artifacts. An object within a field of view is scanned, preferably simultaneously, along a pair of circular source scanning trajectories spaced a distance selected to minimize the amount of missing data. A procedure is disclosed for calculating the spacing distance between the scanning trajectories which minimizes the amount of missing data. In one embodiment, a pair of cone beam x-ray sources are employed and a corresponding pair of two-dimensional array detectors. In order to reduce interference caused by x-rays from one source interacting with the detector corresponding to the other source, the cone beam x-ray sources are angularly offset, for example by 90°.

16 Claims, 10 Drawing Sheets

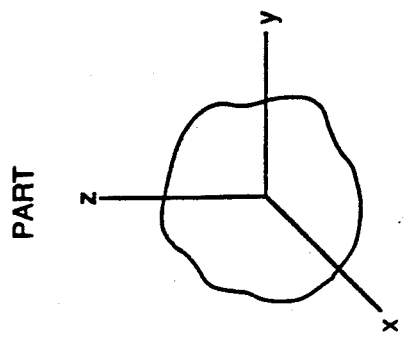
FIG. 2a PART
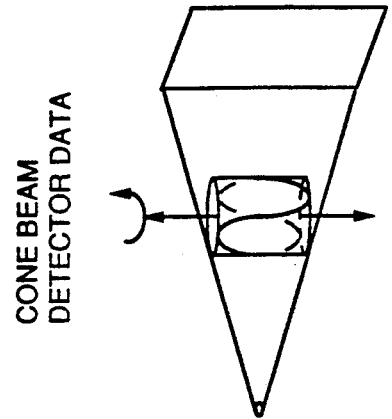
FIG. 2b CONE BEAM DETECTOR DATA
$$X(\theta) = \int f(r,\theta,z_0)\,dr$$
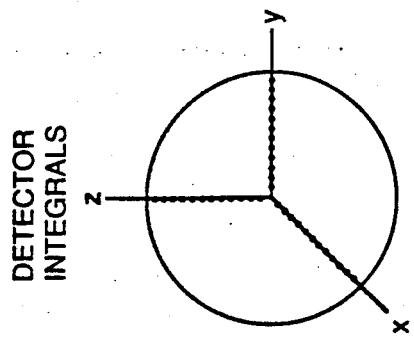
FIG. 2c DETECTOR INTEGRALS
$$\int X(\theta)\,d\theta = \int\!\!\int f(r,\theta,z_0)\,dr\,d\theta$$
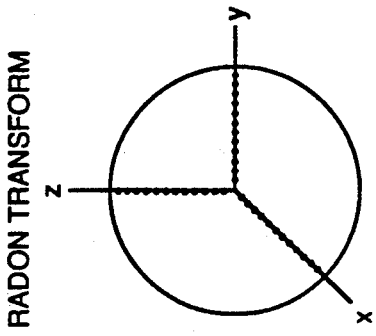
FIG. 2d RADON TRANSFORM
$$\int\!\!\int f(r,\theta,z_0)\,r\,dr\,d\theta$$
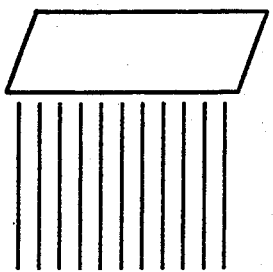
FIG. 2e PARALLEL BEAM DETECTOR DATA
$$\hat{X}(\theta) = \int f(x,y,z)\,ds$$
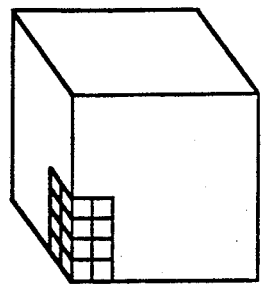
FIG. 2f 3D CT IMAGE
$$\hat{f}(x,y,z)$$

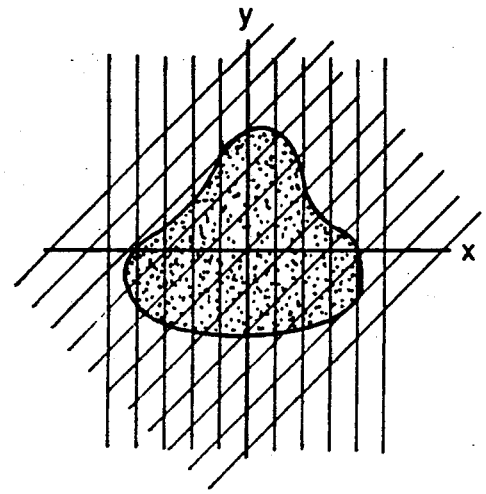 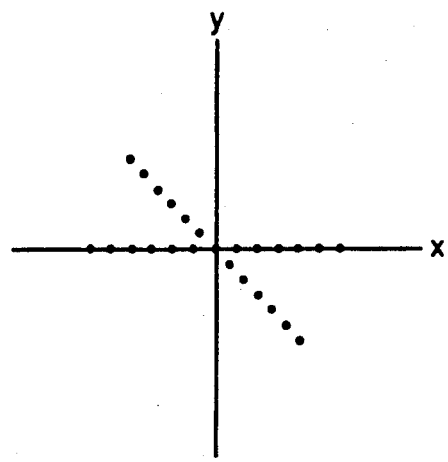
FIG. 4a  FIG. 4b
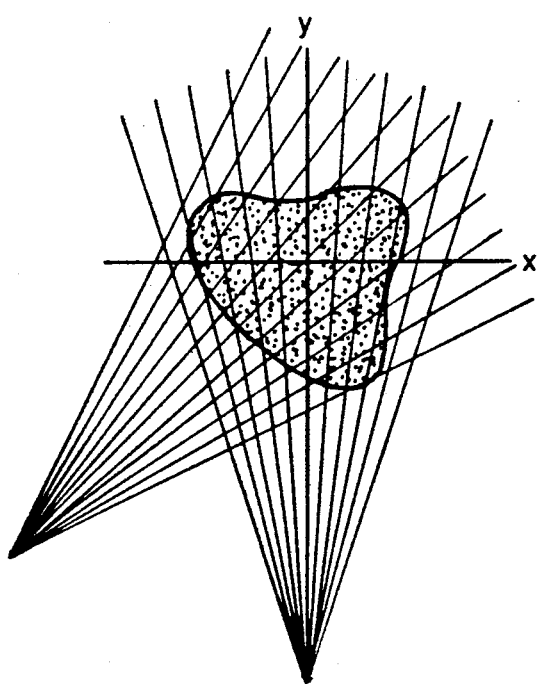 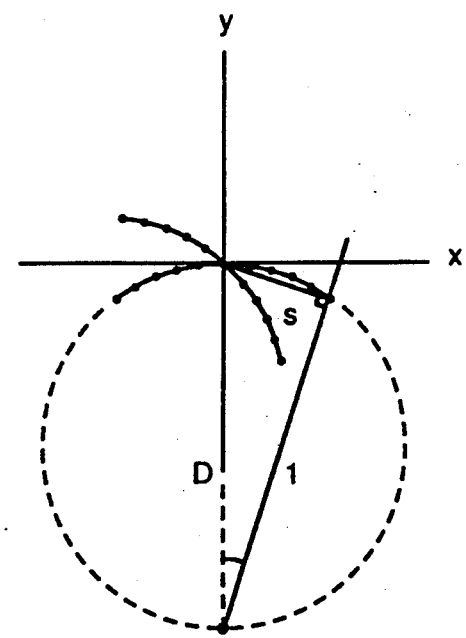
FIG. 5a  FIG. 5b

DUAL PARALLEL CONE BEAM CIRCULAR SCANNING TRAJECTORIES FOR REDUCED DATA INCOMPLETENESS IN THREE-DIMENSIONAL COMPUTERIZED TOMOGRAPHY

BACKGROUND OF THE INVENTION

The present invention relates generally to threedimensional (3D) computerized tomography (CT) and, more particularly, to methods and systems for reducing the amount of missing data when cone beam geometry is employed.

In conventional computerized tomography for both medical and industrial applications, an x-ray fan beam and a linear array detector are employed. Two-dimensional (2D) imaging is achieved. While the data set is complete and image quality is correspondingly high, only a single slice of an object is imaged at a time. When a 3D image is required, a "stack of slices" approach is employed. Acquiring a 3D data set one 2D slice at a time is inherently slow. Moreover, in medical applications, motion artifacts occur because adjacent slices are not imaged simultaneously. Also, dose utilization is less than optimal, because the distance between slices is typically less than the x-ray collimator aperture, resulting in double exposure to many parts of the body.

One approach to acquiring a 3D data set simultaneously is described in the literature: Richard A. Robb, Arnold H. Lent, Barry K. Gilbert, and Aloysius Chu, "The Dynamic Spatial Reconstructor", J. Med. Syst., Vol. 4, No. 2, pp. 253–288 (1980). The Dynamic Spatial Reconstructor employs twenty-eight x-ray sources and twenty-eight x-ray imaging systems in a synchronous scanning system to acquire data for a conventional "stack of slices" reconstruction all at once. The actual geometry is a stack of twenty-eight cone beams scanning twenty-eight respective cylindrical volumes, with area detectors employed to acquire 240 adjacent video lines of data for each slice. However, the data is analyzed as though it is from a stack of fan beam projections, stacked in an axial direction, using conventional 2D reconstruction algorithms. Consistent with this approach, in the Dynamic Spatial Reconstructor the divergence of the x-ray beam above and below the central slice of each cylindrical volume is only ±4.

In a system employing true cone beam geometry, a cone beam x-ray source and a 2D area detector are employed. An object is scanned, preferably over a 360° angular range, either by moving the x-ray source in a scanning circle around the object, while keeping the 2D area detector fixed with reference to the source, or by rotating the object while the source and detector remain stationary. In either case, it is relative movement between the source and object which effects scanning. Compared to the conventional 2D "stack of slices" approach to achieve 3D imaging, the cone beam geometry has the potential to achieve rapid 3D imaging of both medical and industrial objects, with improved dose utilization.

The cone beam geometry for 3D imaging has been discussed extensively in the literature, as represented by the following: M. Schlindwein, "Iterative three-Dimensional Reconstruction from Twin-Cone Beam Projections", IEEE Trans. Nucl.Sci., Vol. NS-25, No. 5, pp. 1135–1143 (October 1978); Gerald N. Minerbo, "Convolutional Reconstruction from Cone-Beam Projection Data", IEEE Trans. Nucl. Sci., Vol. NS-26, No. 2, pp. 2682–2684 (April 1979); Heang K. Tuy, "An Inversion Formula for Cone-Beam Reconstruction", SIAM J. Math., Vol. 43, No. 3, pp. 546–552 (June 1983); L. A. Feldkamp, L. C. Davis, and J. W. Kress, "Practical Cone-Beam Algorithm", J. Opt. Soc. Am. A., Vol. 1, No. 6, pp. 612–619 (June 1984); Bruce D. Smith, "Image Reconstruction from Cone-Beam Projections: Necessary and Sufficient Conditions and Reconstruction Methods", IEEE Trans. Med. Imag., Vol. MI-44, pp. 14–25 (March 1985); and Hui Hu, Robert A. Kruger, and Grant T. Gullberg, "Quantitative Cone-Beam Construction", SPIE Medical Imaging III: Image Processing, Vol. 1092, pp. 492–501 (1989).

A typical scanning and data acquisition configuration employing cone-beam geometry is depicted in FIG. 1. An object 20 is positioned within a field of view between a cone beam x-ray point source 22 and a 2D detector array 24, which provides cone beam projection data. An axis of rotation 26 passes through the field of view and object 20. For purposes of analysis, a midplane 28 is defined which contains the x-ray point source 22 and is perpendicular to the axis of rotation 26. By convention, the axis of rotation 26 is referred to as the z-axis, and the intersection of the axis of rotation 26 and the midplane 28 is taken as the origin of coordinates. x and y axes lie in the midplane 28 as indicated, and the (x,y,z) coordinate system rotates with the source 22 and detector 24. For scanning the object 20 at a plurality of angular positions, the source 22 moves relative to the object 20 and the field of view along a circular scanning trajectory 30 lying in the midplane 28, while the detector 24 remains fixed with respect to the source 22.

Thus, in the configuration of FIG. 1, data are acquired at a number of angular positions around the object by scanning the source and detector along the single circular scanning trajectory 30 (or equivalently rotating the object while the source and detector remain stationary). However, as demonstrated in the literature (e.g. Smith, 1985, above), and as described in greater detail hereinbelow, the data set collected in such a single scan is incomplete. In typical systems, the fraction of missing data can range from 1% to 5% or more, with non-uniform missing data distribution. Missing data introduces artifacts during image reconstruction, resulting in images which can be inadequate for medical diagnosis or part quality determination purposes.

Smith, 1985, above has shown that a cone beam data set is complete if there is a point from the x-ray source scanning trajectory on each plane passing through the object of interest (with the assumptions that the detector is locked in position relative to the source and large enough to span the object under inspection). A configuration suggested by Minerbo (1979, above) and Tuy (1983, above), which Smith points out satisfies his condition for data completeness, is to employ two circular source scanning trajectories which are perpendicular to each other. Such a scanning configuration is however difficult to implement as a practical matter.

SUMMARY OF THE INVENTION

Accordingly, it is an object of the invention to provide a configuration for cone beam 3D CT imaging which minimizes the incompleteness of the data set acquired in a single scan of the object, while providing fast data acquisition to minimize motion artifacts.

Briefly, and in accordance with one aspect of the invention, a scanning and data acquisition method for three-dimensional computerized tomography (CT) imaging of an object within a field of view includes the steps of defining a pair of circular source scanning trajectories centered on a rotation axis passing through the field of view and lying in spaced parallel planes perpendicular to the rotation axis. The source scanning trajectories are spaced a distance selected to minimize the amount of missing data. The method further includes employing at least one cone beam x-ray source and at least one corresponding two-dimensional array detector positioned with reference to the source and with reference to the field of view to scan the object at a plurality of relative angular positions along the source scanning trajectories to acquire cone beam projection data.

Preferably scanning along the pair of source scanning trajectories is accomplished simultaneously, in which case the method includes the step of providing a pair of cone beam x-ray sources respectively on the pair source scanning trajectories, and corresponding two-dimensional array detectors positioned with reference to the x-ray sources and the field of view for obtaining cone beam projection data. The object is scanned at a plurality of angular positions by moving the sources along the scanning trajectories relative to the object. Preferably, scanning is through 360° of angular positions.

In order to reduce interference caused by x-rays from one source interacting with the detector corresponding to the other source, the method includes angularly offsetting the cone beam x-ray sources, such as angularly offsetting the x-ray sources by approximately 90.

In the case of a spherical field of view of radius r centered on an origin located on the rotation axis, the method includes a step of locating the source scanning trajectories in spaced parallel planes intersecting the rotation axis at respective distances $\pm \frac{3}{4}r$ from the origin.

Alternatively, one of the source scanning trajectories may be located in a plane where it is desired to obtain exact two-dimensional computerized tomography data. The location of the other source scanning trajectory is then selected to minimize the amount of missing data.

In accordance with another aspect of the invention, a scanning and data acquisition system for three-dimensional computerized tomography (CT) image of an object within a field of view includes a pair of cone beam x-ray sources, and a pair of two-dimensional array detectors respectively corresponding to the sources and positioned with reference to the source and the field of view for obtaining cone beam projection data. A scanning element is provided for effecting relative motion between the sources and the object. The sources move relative to the object along respective circular scanning trajectories centered on a rotation axis passing through the field of view and lying in spaced parallel planes perpendicular to the rotation axis so as to acquire cone beam projection data with the sources at a plurality of angular positions on the respective scanning trajectories.

The source scanning trajectories are spaced a distance selected to minimize the amount of missing data. In the case of an object within a spherical field of view of radius r centered on the origin, the source scanning trajectories are located in spaced parallel planes intersecting the rotation axis at respective distances $\pm \frac{3}{4}r$ from the origin.

Alternatively, one of the source scanning trajectories may be located in a plane where it is desired to obtain exact two-dimensional computerized tomography data, and the other source scanning circle is located where the amount of missing data is minimized.

In order to reduce interference caused by x-rays from one source interacting with the detector corresponding to the other source, the cone beam x-ray sources are angularly offset, for example by 90°.

Thus, by the present invention, a 3D cone beam CT imaging configuration is provided which can acquire a high quality data set in the same time as is required for a single slice in a conventional 2D CT Scanner, with minimal motion artifacts.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIGS. 2a, 2b, 2c, 2d, 2e and 2f are diagrams depicting the Radon transform approach to 3D CT imaging;

FIGS. 4a and 4b depict Radon space filling in the case of 2D parallel beam CT;

FIGS. 5a and 5b depict Radon space filling in the case of 2D fan beam CT;

DETAILED DESCRIPTION

Figure 1:
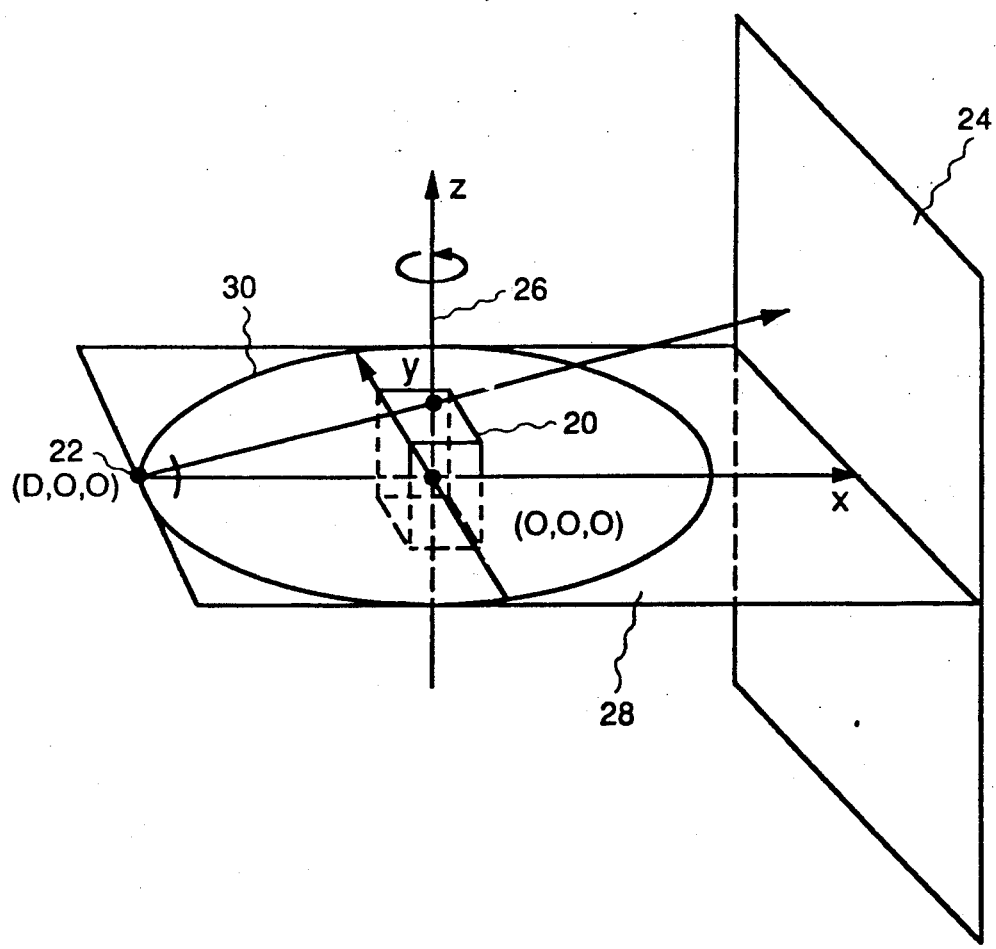
FIG. 1, referred to hereinabove, represents conventional cone beam scanning geometry for 3D CT.

Since the present invention is directed to reducing the data set incompleteness in the prior art cone beam scanning geometry of FIG. 1, what is meant by data set incompleteness will next be defined and described, followed by a description of methods and systems in accordance with the invention.

Data set completeness can be defined most clearly and rigorously in terms of the Radon transform approach to 3D imaging, represented in FIGS. 2a through 2f. The object itself is defined in terms of its x-ray attenuation coefficient f(x,y,z) (FIG. 2a). The measured cone beam projection data then corresponds to a line integral of this function over the radial direction $X(\theta) = \int f(r,\theta, Z_o) dr$ (FIG. 2b). The line integrals of the detector data (also known as detector integrals) are given by $\int X(\theta) d\theta = \int \int f(r,\theta, Z_o) dr\, d\theta$ (FIG. 2c). In the parallel beam case, these detector integrals are simply equal to the Radon transform of the object. In the cone beam case, however, the Radon transform is given instead by $\int \int f(r, \theta, Z_o) r\, dr\, d\theta$ (FIG. 2d). The additional factor of r in the Radon transform integral results from the Jacobian of the coordinate transformation from Cartesian to polar coordinates. As depicted in FIGS. 2e and 2f, an inverse Radon transform procedure reconstructs a 3D CT image from the detector integrals. Since direct inverse Radon transformation requires planar integrals of the object as input, an intermediate step of converting cone beam detector integrals to planar integrals may be employed, although a variety of reconstruction techniques are available, as is apparent from the literature.

It is significant to note that the data set is complete if it provides data at every point in Radon transform space; i.e., Radon space is filled with data over the region of support corresponding to the field of view in real space within which the object of interest fits. Therefore, the filling of Radon space by various scanning configurations is of significant interest. (In addition, it can be shown that if detector integral space is filled over the region of support for the object, the data set is complete.)

Figure 3:
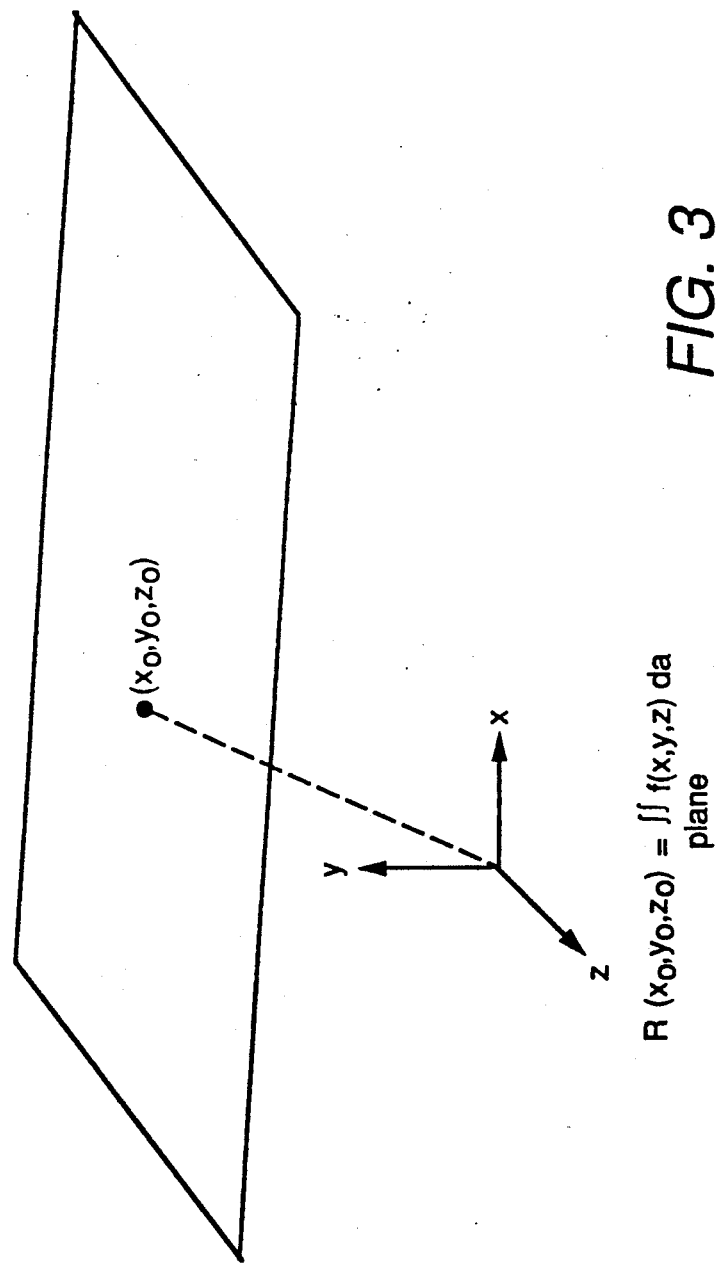
FIG. 3 is a representation of the 3D Radon transform of an object at a given point.

As depicted in FIG. 3, the Radon transform of an object at a point $X_0, Y_0, Z_0$ is given by the area integral of the x-ray attenuation coefficient over the plane passing through $X_0, Y_0, Z_0$ that is perpendicular to the line from the origin to $X_0, Y_0, Z_0$, and can be expressed as $$R(x_o, y_o, z_o) = \int\int_{plane} f(x, y, z) da$$

In 2D, the situation is similar, except that the integral is over a line, not over a plane.

Any scanning and data acquisition configuration provides data over some volume of Radon space. Described next with reference to FIGS. 4a through 7b are regions in Radon space which are filled and which are not for various 2D and 3D scanning configurations.

FIGS. 4a and 4ib represent Radon space filling for 2D parallel beam CT. The x-ray paths for two view angles are shown in FIG. 4a, and the resulting points in Radon space are shown in FIG. 4b. For each point in Radon space, a line is extended from the origin to the point of interest, and the x-ray intensity is integrated over a line passing through that point and perpendicular to the line to that point from the origin. Such points are shown in FIG. 4b for each ray depicted in FIG. 4a, for each of two view angles.

The situation for fan beam data acquisition is similar (FIGS. 5a and 5b), but here the ray paths diverge from the x-ray source, and the geometry is slightly more complicated. The procedure is the same, however. By way of example, the extreme right-hand ray of the fan beam is analyzed in FIG. 5b. The perpendicular line to the ray is labeled "s". It may be noted that the point of Radon space of interest forms a right triangle with the origin and the x-ray source point. (It is the same point that would be determined in parallel beam geometry for a view angle orientation of one-half the fan angle.) This is generally true for any point in Radon space acquired with the detector in this position. Therefore, by geometry, the points in Radon space lie on the arc of a circle whose diameter is the source to center of rotation distance. Similar arcs are constructed for each view angle position around the object. It can be appreciated from this construct that complete data is provided by rotating source and detector around the object through an angle of 180° plus the fan angle.

Figures 6A, 6B:
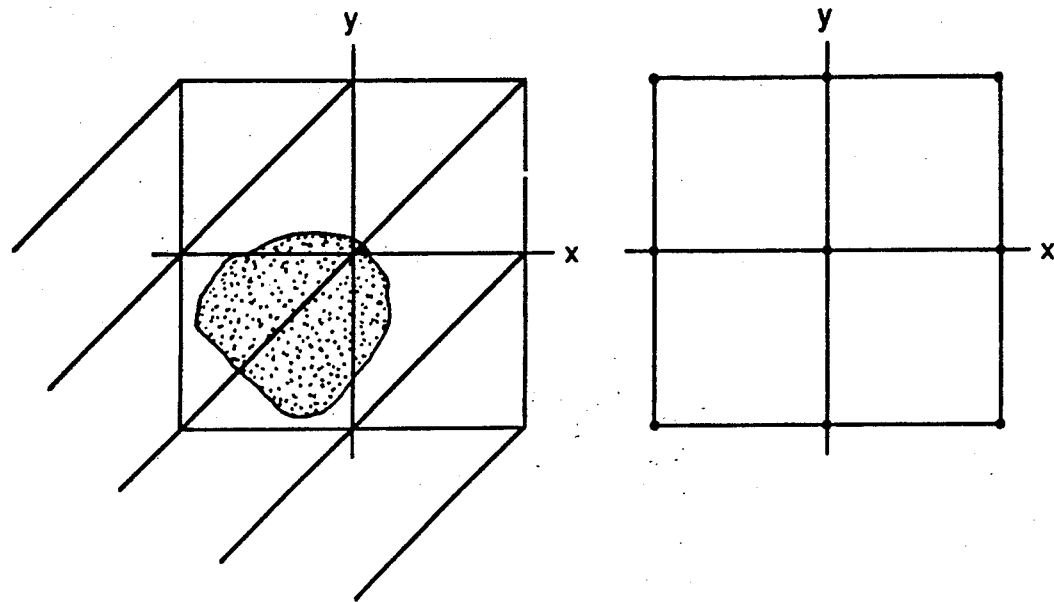
FIGS. 6a and 6b depict Radon space filling in the case of 3D parallel beam CT.

The parallel beam case for 3D is represented in FIGS. 6a and 6b. Here, the x-ray attenuation measurement corresponds to integration in the z direction, and line integrals of the detector data are taken at other orientations in the detector plane to fill in Radon space on a single plane passing through the object. For example, the point in Radon space at $x=0, y=y_o$ corresponds to the detector integral over points in the detector a distance yo above the x,z plane. Points off axis in Radon space correspond to detector integrals along straight lines with various slopes in detector space. For example, the point at $x=c, y=c$ in Radon space corresponds to detector integrals along lines with slope $-45°$ with respect to the x axis and a distance $\sqrt{2}c$ from the origin.

Figures 7A, 7B:
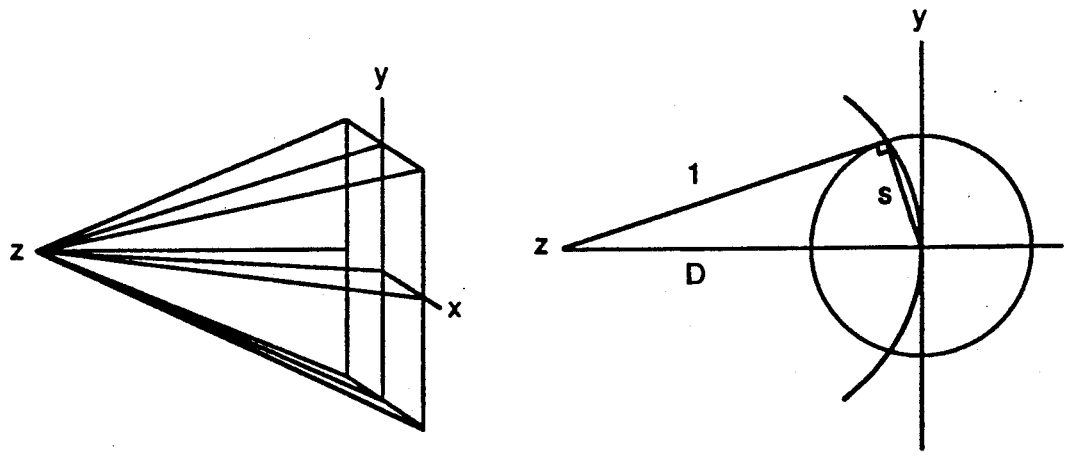
FIGS. 7a and 7b depict Radon space filling in the case of 3D cone beam CT.

The particularly relevant cone beam case in 3D is similarly represented in FIGS. 7a and 7b. Corresponding to FIGS. 7a and 7b are prior art FIG. 1, described hereinabove; prior art FIG. 8, which depicts a single circular source scanning trajectory 32 around a spherical field of view 34 of radius R within which an object to be scanned fits; and prior art FIG. 9, which depicts in cross-section the intersection of a sphere 36 of equal radius in Radon space comprising the region of support for the spherical field of view 34 with a toric volume 38 representing the region in Radon space for which data are available. In FIG. 9, the diameter of each side of the toric volume 38 is equal to the source to axis of rotation distance D.

In FIGS. 7a and 7b, the exemplary point shown in Radon space corresponds to the detector integral along the top line of the detector data. The geometry is similar to the fan beam case in 2D. The points in Radon space for all detector line integrals at a single view angle correspond to a section of a sphere with diameter equal to the source to center of rotation distance. A new spherical shell of data is created at each view angle, and for a 360° scan, the available data falls inside the toric volume 38 (FIG. 9).

Thus, as represented in FIG. 9, in Radon space data for reconstruction are available at those points within the sphere 36 where the sphere intersects the toric volume 38, as indicated by the word "data". As indicated by the words "missing data", data are absent for points on the top and bottom of the Radon sphere 36 because these points correspond to planes parallel and near parallel to the x,y plane and data for these planes are not available because of the cone beam nature of the x-ray source. The region of missing data narrows as z approaches the midplane, and for z=0 (on the midplane), all the required data are available.

As shown by Smith, 1985, above, a cone beam data set is complete if there is a point from the x-ray source scanning trajectory on each plane passing through the object of interest. (The detector is assumed to be locked in position relative to the source and large enough to span the object under inspection.) Relating this to FIG. 8 where the circular source scanning trajectory 32 surrounds the exemplary field of view 34, by Smith's criterion the trajectory 32 is incomplete because a number of horizontal and near-horizontal planes pass through the region of support of the object (i.e. the field of view 34) without intersecting the source scanning trajectory 36. These planes are exactly those that correspond to the missing data in Radon space in FIG. 9. When applying Smith's criterion, it may be noted that, for large z, the number of planes through the object not intersecting the source scanning trajectory is relatively large, and the number decreases as z decreases. This same behavior is noted in Radon space, as shown in FIG. 9. It may also be noted that vertical planes passing through the object do intersect the scanning trajectory, and that, as the diameter of the trajectory increases relative to the diameter of the object, the amount of missing data (the number of planes that do not intersect the scanning trajectory) decreases.

Relating the foregoing to actual practice, the following Table I shows the amount of missing data for two general cases (D=r and D=2r) and for several actual inspection systems manufactured by General Electric Company. The general case D=r does not represent a practical system, as the source scanning circle (defined by the source to rotation axis distance D) would be on the outer boundary of the field of view (defined by the radius r), and an extremely large detector would be required to span the object, but is included to illustrate the trend. In the GEMS CT9800 scanning geometry, for example, approximately 5% of the required data for 3D imaging is unavailable from a single scan of a 2D detector. In the ICT system, because of the smaller field of view, the fraction of missing data is approximately 1%.

Although these fractions of mission data are generally rather small, missing data is non-uniformly distributed over the image.

In accordance with the invention, a dual parallel scanning trajectory significantly reduces the amount of missing data and yet is practical to implement.

Figure 8:
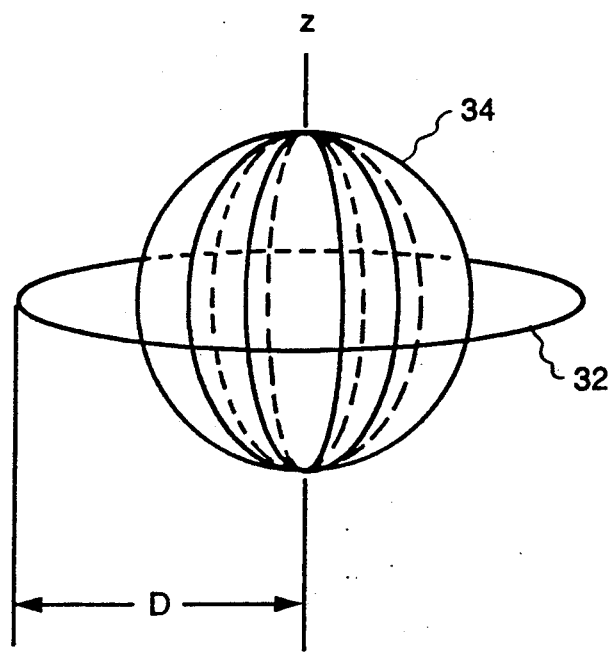
FIG. 8 depicts a prior art circular scanning trajectory corresponding to FIG. 1.
Figure 9:
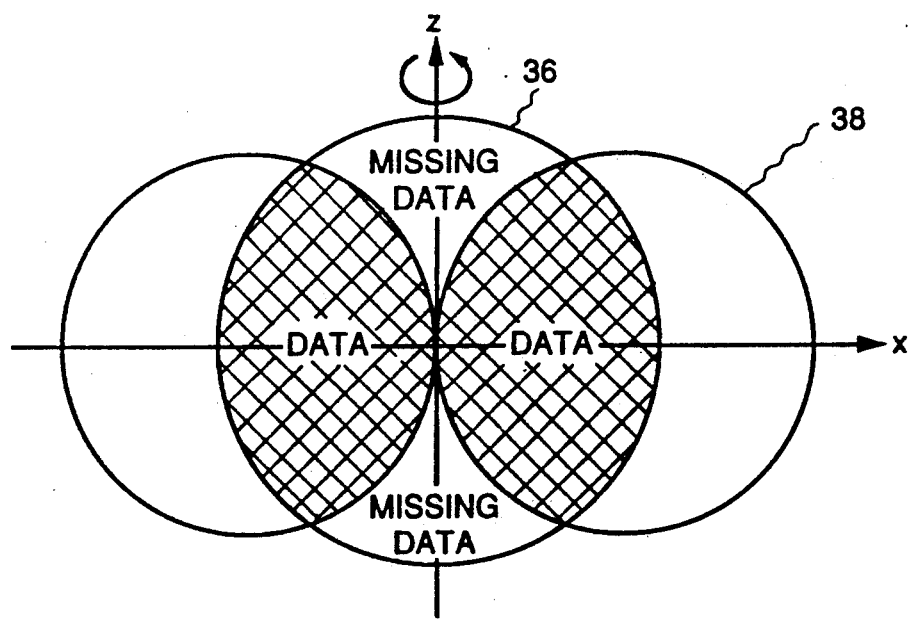
FIG. 9 depicts regions of available data and missing data in Radon space when the prior art scanning configuration of FIGS. 1 and 8 is employed.
Figure 12:
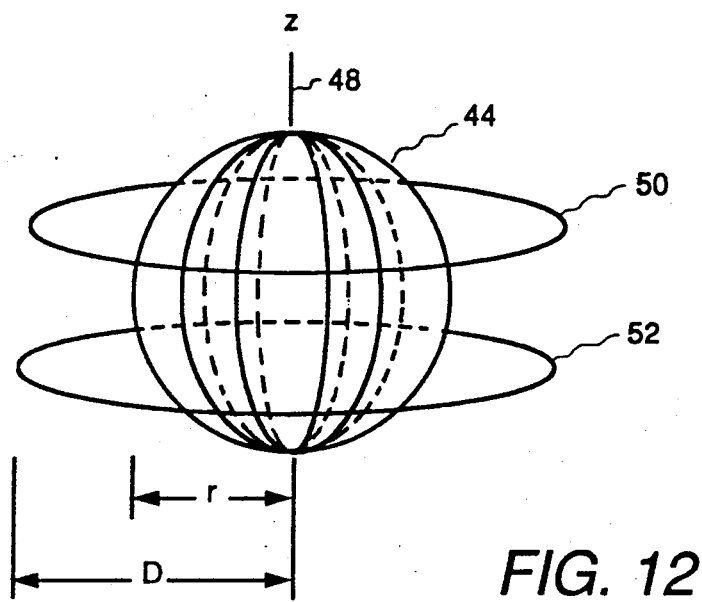
FIG. 12 depicts a dual parallel circular scanning trajectory configuration in accordance with the invention.
Figure 13:
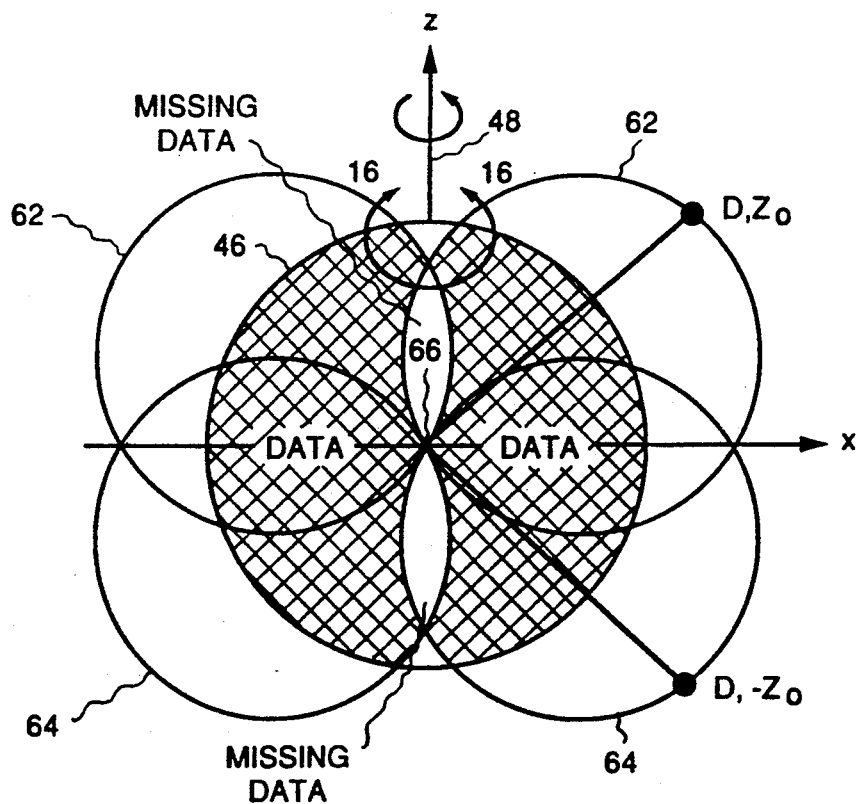
FIG. 13 depicts regions of available data and missing data in Radon space when the scanning configuration of FIG. 12 is employed.

FIG. 12, which may be contrasted with prior art FIG. 8, generally depicts the scanning geometry of the invention. FIG. 13, which may be contrasted with prior art FIG. 9, depicts Radon spacing filling, from which it is apparent that data incompleteness is significantly reduced. Moreover, data from the two scanning paths can be acquired simultaneously. Thus motion artifacts are essentially no worse than in a single slice 2D CT image, and substantially reduced from those present in a "stack of slices" reconstruction where scanning times can be quite long.

Figure 14:
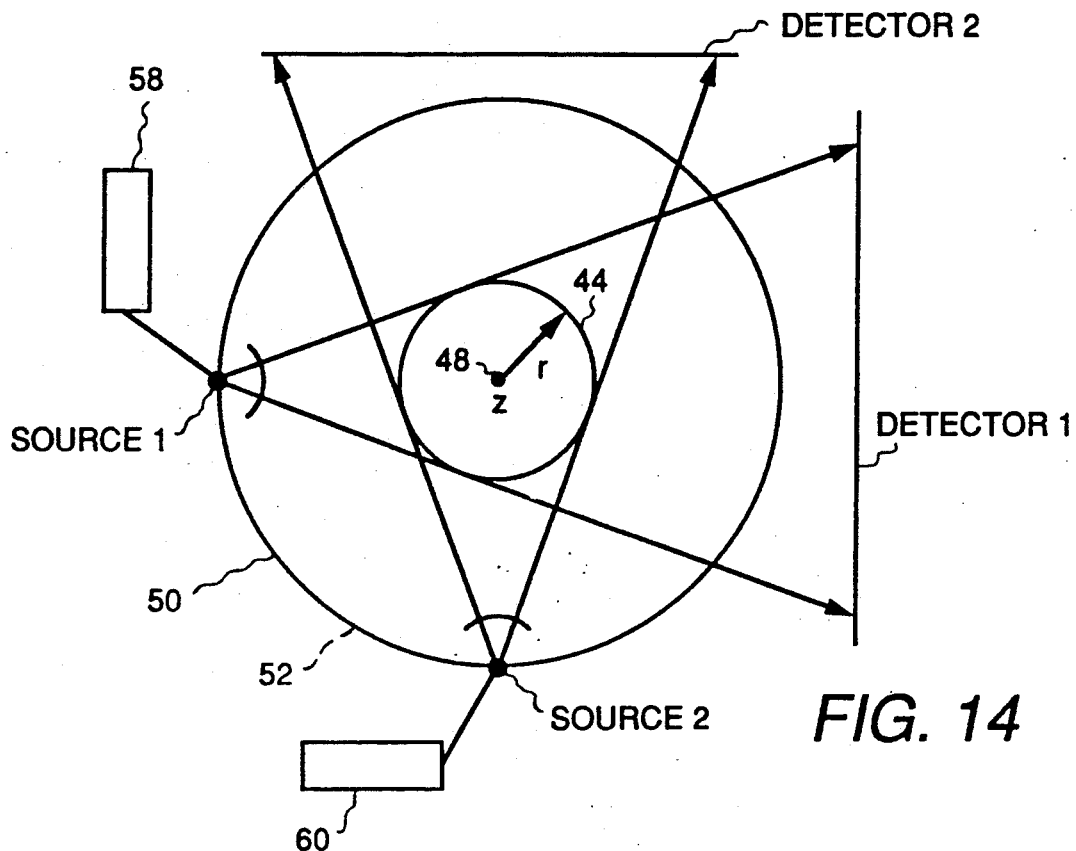
FIG. 14 is a top view of a system embodying the scanning configuration of the invention.
Figure 15:
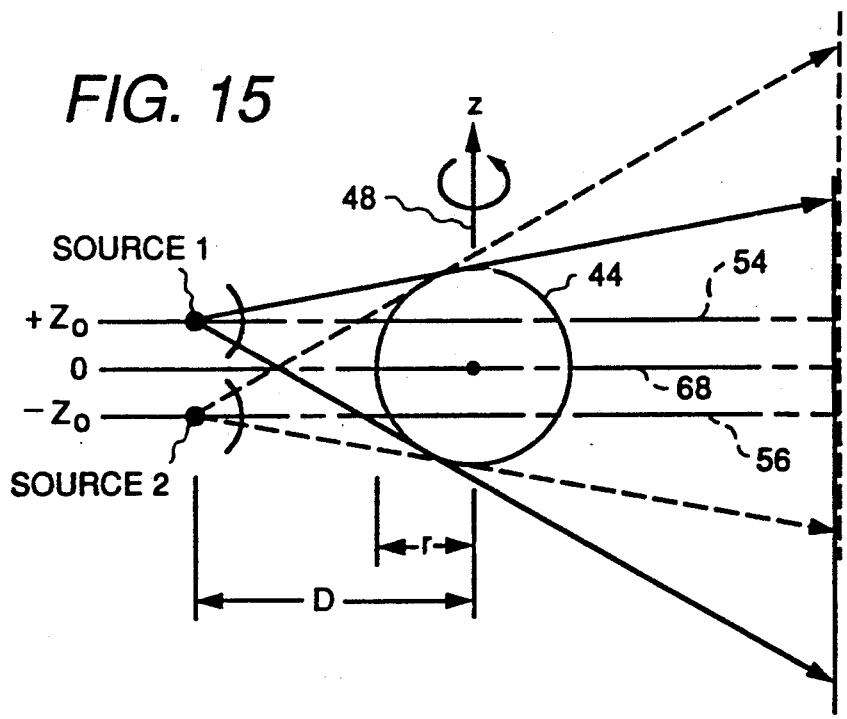
FIG. 15 is a modified side view of a system embodying the scanning configuration of the invention, modified to better illustrate the vertical offset between the parallel circular scanning trajectories.

A practical implementation of the geometry of FIG. is depicted in FIGS. 14 and 15. FIG. 14 is a top view, while FIG. 15 is a modified side view.

Considering the dual parallel scanning trajectory configuration in detail, an object to be imaged (not shown) is within a representative spherical field of view 44 (corresponding to a Radon space sphere 46 of equal diameter in FIG. 13), through which a rotation axis 48 (z axis) passes. A pair of circular source scanning trajectories 50 and 52 (superimposed in the top view of FIG. 14) are centered n the rotation axis 48, and respectively lie in spaced parallel planes 54 and 56 (FIG. 15) perpendicular to the rotation axis 48. As described in greater detail hereinbelow, the parallel planes 54 and 56 and thus the source scanning trajectories 50 and 52 are spaced or offset a distance selected to minimize the amount of missing data. (The side view of FIG. 15 is modified by repositioning Source 2 so as to more clearly depict the vertical offset.)

A pair of cone beam x-ray sources Source 1 and Source 2 are respectively located on the scanning trajectories 50 and 52, and corresponding two-dimensional array detectors Detector 1 and Detector 2 are positioned with reference to the x-ray source Source 1 and Source 2 and with reference to the field of view 44 for

TABLE I

| | | | 3D CT Single Source Circle | | | |
|---|---|---|---|---|---|---|
| System | Source to Center | FOV Radius | Half Cone Angle | Yinter | Available Data (%) | Missing Data (%) |
| D = r | r | r | 90° | — | $3\frac{\pi}{16} = 58.9\%$ | |
| D = 2r | 2r | r | 30° | $\frac{\sqrt{3}}{2} r = .866r$ | 92.1% | 7.9% |
| XIM | 16.9" | 1.28" | 4.3° | 1.276" | 99.8% | .2% |
| ICT Family | 33" | 6" | 10.5° | 5.90" | 99% | 1% |
| CT9800 (48 cm) | 63 cm | 24 cm | 22.4° | 22.2 cm | 95.5% | 4.5% |
| CT9800 (35 cm) | 63 cm | 17.5 cm | 16.1° | 16.8 cm | 97.6% | 2.4% |

Figure 10:
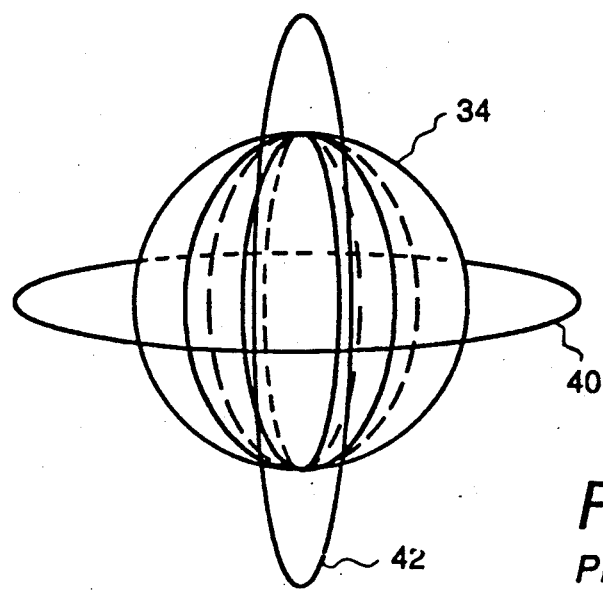
FIG. 10 depicts a prior art dual perpendicular source scanning trajectory configuration.
Figure 11:
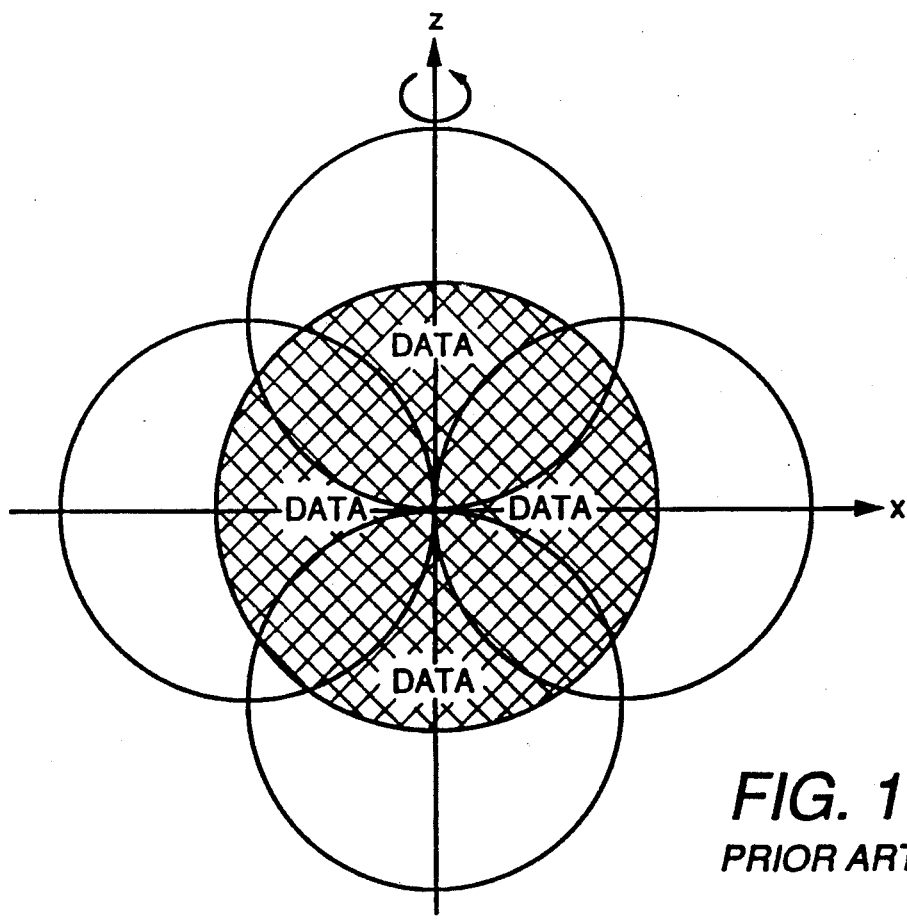
FIG. 11 depicts regions of available data in Radon space when the prior art scanning configuration of FIG. 10 is employed.

As noted above, Minerbo (1979) and Tuy (1983) have suggested a dual perpendicular source circle scanning trajectory, as is represented in prior art FIG. 10 by two perpendicular circles 40 and 42. For objects that fit inside this trajectory, complete data is available. The corresponding filling of Radon space is represented in FIG. 11. However, for many industrial applications, the dual perpendicular scanning trajectory is difficult to implement because it requires complex fixturing or regripping of the part during the scan.

obtaining cone beam projection data. The detectors Detector 1 and Detector 2 are fixed with reference to the sources Source 1 and Source 2, and scanning is accomplished in a conventional manner by moving the sources Source 1 and Source 2 along the scanning circles 50 and 52 relative to the object and the field of view 44. Scanning is preferably over a 360° angular range. Since it is relative movement which effects scanning, either the object (and with it the field of view 40) can be rotated while the sources Source 1 and Source 2 and the detectors Detector 1 and Detector 2 remain stationary, or the object and field of view 40 can remain stationary while the sources and detectors move. Generalized scanning elements 58 and 60 represent the actual hardware whereby the object is scanned at a plurality of relative angular positions.

As represented in FIG. 14, in order to reduce the interference of x-rays from one source interacting with the detector corresponding to the other source, the two sources Source 1 and Source 2 are angularly offset, for example by 90°. Other angular offsets may be employed, chosen for purposes of scatter reduction, mechanical convenience, or other system considerations.

Relating this geometry to Radon space filling, FIG. 13, for the exemplary spherical field of view 44, depicts in cross-section the corresponding sphere 46 of equal radius in Radon space. Superimposed in FIG. 13 are two available data circles respectively defining toric volumes 62 and 64 corresponding to the two source scanning circles 50 and 52. Available data and missing data areas are indicated. In FIG. 13, an x-axis intersects the z-axis or rotation axis 40 at an origin 66, which lies on a midplane 68 (FIG. 15).

By definition, each of the available data circles in FIG. 13 defining the toric volumes 62 and 64 intersect the origin 66. The diameter of the toric volume-defining circles in FIG. 13 is determined by the source to center of rotation distance D (FIG. 15). Thus in FIG. 13 the two points D,$z_o$ and D,$-z_o$ represent the intersection of the scanning trajectories 50 and 52 with the toric volume-defining circles.

Although it is preferably to employ the pair of cone beam x-ray sources Source 1 and Source 2 and the corresponding pair of detectors Detector 1 and Detector 2 so that the two scans can be accomplished simultaneously to minimize motion artifacts, particularly in medical applications, a single cone beam x-ray source and a single two-dimensional array detector may be employed to sequentially scan along the two source scanning trajectories 50 and 52. While this approach takes twice as long for scanning, it is practical in industrial part-inspection applications. Preferably, the part being inspected is scanned past a stationary source and detector using a 2-axis CNC part manipulator having a vertical translation axis and a rotation axis.

Figure 16:
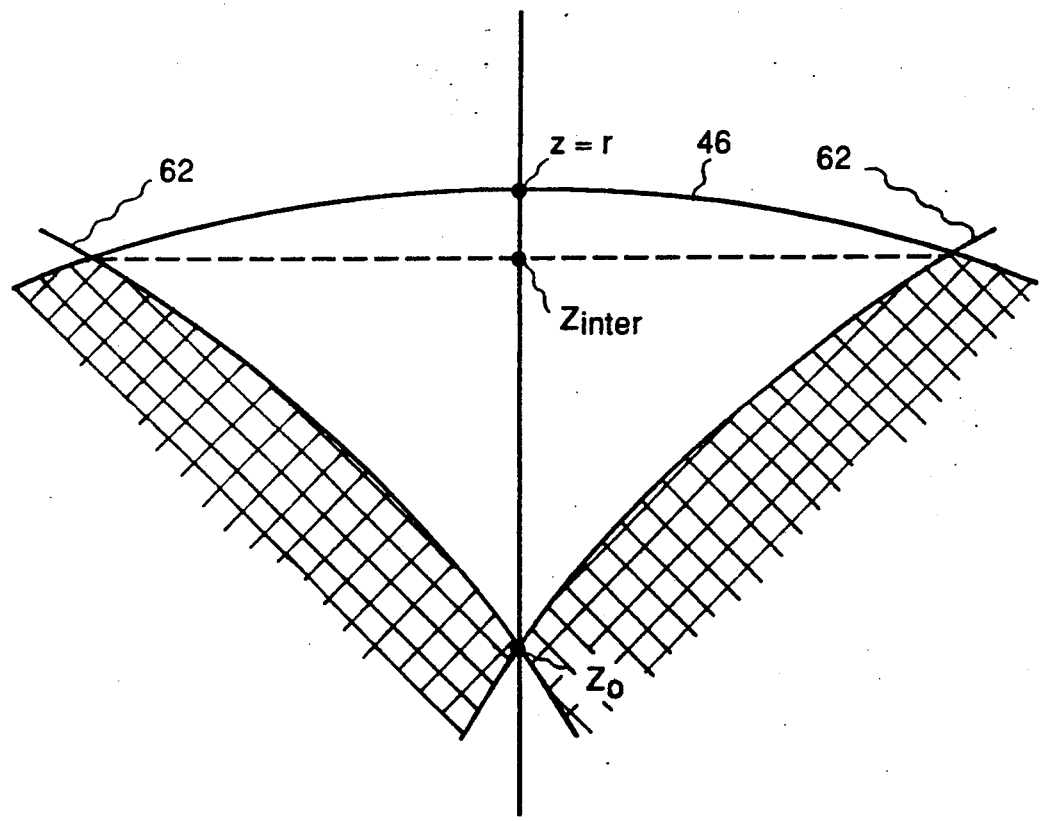
FIG. 16 is an enlargement of the upper portion of FIG. 13.

The manner in which the spacing between the parallel planes 54 and 56 containing the circular source scanning missing data with reference to Radon space filling will now be described with reference to FIG. 13, and with reference to FIG. 16 which is a portion of FIG. 13 enlarged to show detail and nomenclature. This example is for the case of a spherical field of view centered on the origin. However, it will be appreciated that similar calculations can be employed to determine the spacing to minimize missing data for various non-spherical fields of view, such as for cylindrical fields of view.

First an object field of view is selected, defined by its radius r centered on the origin. This also defines the Radon space sphere of required dat. The volume in Radon space is $$V = \frac{4}{3}\pi r^3.$$

Next, the source-to-center of rotation distance D is selected or determined. This then defines the Radon space toric volume of available data.

Finally, the distance above and below the origin ($\pm z$) for the two source scanning trajectories are selected, based on calculation to minimize the amount of missing data. While a direct calculation may be employed, an interative approach is simpler.

Thus, for an interation, a z-axis height $z_o$ is selected for the scanning trajectory 50. (Since the geometry is symmetrical, the z-axis height for the scanning trajectory 52 is $-z_o$.) In the x,z plane a source point is defined $x=D, z=z_o$.

In two dimensions, the intersection of the Radon space toric volume with the z-axis is calculated. The general equation for the available data circle is $(x-x_c)+(z-z_c)^2=P^2$, for center $x_c,z_c$, and radius Phu 2. Here the center is at X $$x_c = \frac{D}{2}, z_c = \frac{z_o}{2}.$$

Also $$P^2 = \left(\frac{D}{2}\right)^2 = \left(\frac{z_o}{2}\right)^2.$$

(Note that P is not equal to R, the radius of the required data sphere (a required data circle in two dimensions). The equation then is $$\left(x - \frac{D}{2}\right)^2 + \left(z - \frac{z_o}{2}\right)^2 = \left(\frac{D}{2}\right)^2 + \left(\frac{z_o}{2}\right)^2.$$

The origin (0,0), the source point (D,$z_o$) and the point (0,$z_o$) all satisfy the above equation.

Then the intersection in Radon space of the toric volume with the region of support sphere is calculated:

$$Z_{inter} = \frac{r^2 z_0 \pm Dr\sqrt{D^2 + z_o^2 - r^2}}{D^2 + z_o^2}$$

Next, missing data in the three regions is calculated, and the results are summed:

$$V_1 = 2\pi \int_0^{z_o} [f(z)]^2 \, dz$$

$$V_2 = 2\pi \int_{Z_o}^{Z_{inter}} [f(z)]^2 dz$$

$$V_3 = 2\pi \int_{Z_{inter}}^{r} (r^2 - z^2) dz$$

$$V_{missing} = V_1 + V_2 + V_3$$

where $$f(z) = \frac{1}{2}D \pm \sqrt{\frac{1}{4}D^2 + \frac{1}{4}z_o^2 - \left(z - \frac{1}{2}z_o\right)^2}.$$

By iteration it can be determined that the volume of missing data $V_{missing}$ in Radon space is minimized when $Z_o = \frac{3}{4}r$. This turns out to be independent of the source to center of ratio distance D.

Calculated results are shown in the following Table II, which may be contrasted with Table I, above. it is apparent that the fractions of missing data are significantly reduced, in many cases by more than an order of magnitude.

TABLE II

| | 3D CT Single Source Circle | | | | | |
|---|---|---|---|---|---|---|
| System | Source to Center | FOV Radius | Half Cone Angle | Offset | Available Data (%) | Missing Data (%) |
| D = r | r | r | 90° | — | — | — |
| D = 2r | 2r | r | 30° | $\pm \frac{3}{4} r$ | 99.5% | .5% |
| XIM | 16.9" | 1.28" | 4.3° | ±.96" | 99.99% | .01% |
| ICT Family 1 | 33" | 6" | 10.5° | ±4.5" | 99.94% | .06% |
| CT9800 (48 cm) | 63 cm | 24 cm | 22.4° | ±18 cm | 99.73% | .27% |
| CT9800 (35 cm) | 63 cm | 17.5 cm | 16.1° | ±13.125 cm | 99.86% | .14% |

When it is desired to obtain exact 2D CT data for a particular slice, one of the scanning circles is positioned at that location and the location of the other is then selected, employing calculations like the foregoing, to minimize the missing date. While specific embodiments of the invention have been illustrated and described herein, it is realized that modifications and changes will occur to those skilled in the art. It is therefore to be understood that the appended claims are intended to cover all such modifications and changes as fall within the true spirit and scope of the invention.

What is claimed is:

1. A scanning and data acquisition method for three-dimensional computerized tomography (CT) imaging of an object within a field of view, said method comprising;
  defining a pair of circular source scanning trajectories centered on the rotation axis passing through the field of view and lying in spaced parallel planes perpendicular to the rotation axis, the source scanning trajectories being spaced a distance selected to minimize the amount of missing data; and
  employing at least one cone beam x-ray source and at least one corresponding two-dimensional array detector positioned with reference to the at least one source and with reference to the field of view to scan the object at a plurality of relative angular positions along the source scanning trajectories to acquire cone beam projection data.

2. A method in accordance with claim 1, which comprises scanning the object through 360° of relative angular positions.

3. A method in accordance with claim 1, wherein the field of view is a spherical field of view of radius r centered on an origin located one rotation axis, and which comprises:
  locating the source scanning trajectories in spaced parallel planes intersecting the rotation axis at respective distances $\pm \frac{3}{4}r$ from the origin.

4. A method in accordance with claim 1, which comprises locating one of the source scanning trajectories in a plane where it is desired to obtain exact two-dimensional computerized tomography data.

5. A scanning and data acquisition method for three-dimensional computerized tomography (CT) imaging of an object within a field of view, said method comprising:
  defining a pair of circular source scanning trajectories centered on a rotation axis passing through the field of view and lying in spaced parallel planes perpendicular to the rotation axis, the source scanning trajectories being spaced a distance selected to minimize the amount of missing data;
  providing a pair of cone beam x-ray sources respectively on the pair of source scanning trajectories, and providing corresponding two-dimensional array detectors positioned with reference to the x-ray sources and the field of view for obtaining cone beam projection data; and
  moving the sources along the scanning trajectories relative to the object so as to scan the object at a plurality of angular positions.

6. A method in accordance with claim 5, which comprises angularly offsetting the cone beam x-ray sources so as to reduce interference caused by x-rays from one source interacting with the detector corresponding to the other source.

7. A method in accordance with claim 6, which comprises angularly offsetting the sources approximately 90°.

8. A method in accordance with claim 5, which comprises scanning the object through 360° of relative angular positions.

9. A method in accordance with claim 5, wherein the field of view is a spherical field of view of radius r centered on an origin located on the rotation axis, and which comprises:
  locating the source scanning trajectories in spaced parallel planes intersecting the rotation axis at respective distances $\pm \frac{3}{4}r$ from the origin.

10. A method in accordance with claim 5, which comprises locating one of the source scanning trajectories in a plane where it is desired to obtain exact two-dimensional computerized tomography data.

11. A scanning and data acquisition system for three-dimensional computerized tomography (CT) imaging of an object within a field of view, said system comprising:
  a pair of cone beam x-ray sources;
  a pair of two-dimensional array detectors respectively corresponding to said sources and positioned with reference to said sources and the field of view for obtaining cone beam projection data;
  a scanning element for effecting relative motion between said sources and the object, said sources moving relative to the object along respective circular source scanning trajectories centered on a rotation axis passing through the field of view and lying in spaced parallel planes perpendicular to the rotation axis, so as to acquire cone beam projection data with said sources at a plurality of angular positions on the respective scanning trajectories; and the source scanning trajectories being spaced a distance selected to minimize the amount of missing data.

12. A system in accordance with claim 11, wherein said cone beam x-ray sources are angularly offset so as to reduce interference caused by x-rays from one source interacting with the detector corresponding to the other source.

13. A method in accordance with claim 12, wherein said sources are offset approximately 90°.

14. A system in accordance with claim 11, wherein said scanning element is operable to scan through 360° of relative angular positions.

15. A system in accordance with claim 11 for imaging an object within a spherical field of view of radius r centered on a origin located on the rotation axis, wherein the source scanning trajectories are located in spaced parallel planes intersecting the rotation axis at respective distances $\pm \frac{3}{4}r$ from the origin.

16. A system in accordance with claim 11, wherein one of the source scanning trajectories is located in a plane where it is desired to obtain exact two-dimensional computerized tomography data.

* * * * *